(12) United States Patent
Bagley et al.

(10) Patent No.: US 11,850,324 B2
(45) Date of Patent: Dec. 26, 2023

(54) THREE-DIMENSIONAL (3-D) PRINTING INKS MADE FROM NATURAL EXTRACELLULAR MATRIX MOLECULES

(71) Applicant: ADVANCED BIOMATRIX, INC., Carlsbad, CA (US)

(72) Inventors: David Bagley, San Diego, CA (US); Bowman Bagley, Carlsbad, CA (US); Dale Peterson, Carlsbad, CA (US)

(73) Assignee: Advanced Biomatrix, Inc., Carlsbad, CA (US)

( * ) Notice: Subject to any disclaimer, the term of this patent is extended or adjusted under 35 U.S.C. 154(b) by 1111 days.

(21) Appl. No.: 16/341,360

(22) PCT Filed: Oct. 12, 2017

(86) PCT No.: PCT/US2017/056297
§ 371 (c)(1),
(2) Date: Apr. 11, 2019

(87) PCT Pub. No.: WO2018/071639
PCT Pub. Date: Apr. 19, 2018

(65) Prior Publication Data
US 2020/0179563 A1  Jun. 11, 2020

Related U.S. Application Data

(60) Provisional application No. 62/536,727, filed on Jul. 25, 2017, provisional application No. 62/406,977, filed on Oct. 12, 2016.

(51) Int. Cl.
*A61L 27/26* (2006.01)
*B29C 64/188* (2017.01)
*B29C 64/40* (2017.01)
*A61L 27/36* (2006.01)
*B33Y 70/10* (2020.01)
(Continued)

(52) U.S. Cl.
CPC ............ *A61L 27/26* (2013.01); *A61L 27/3633* (2013.01); *B29C 64/188* (2017.08); *B29C 64/40* (2017.08); *B33Y 70/10* (2020.01); *B29K 2089/00* (2013.01); *B33Y 10/00* (2014.12); *B33Y 40/20* (2020.01)

(58) Field of Classification Search
CPC ....................................................... A61L 27/26
See application file for complete search history.

(56) References Cited

U.S. PATENT DOCUMENTS

| | | | |
|---|---|---|---|
| 5,316,942 A | 5/1994 | Fink | |
| 2015/0050686 A1* | 2/2015 | Sheth | C12M 33/00 435/29 |
| 2015/0375453 A1 | 12/2015 | Yost et al. | |

FOREIGN PATENT DOCUMENTS

| | | |
|---|---|---|
| CN | 104068945 A | 10/2014 |
| KR | 20150059132 | 5/2015 |

(Continued)

OTHER PUBLICATIONS

Dababneh et al (J. Manuf. Sci. Eng. Dec. 2014, 136(6): 061016). (Year: 2014).*

(Continued)

*Primary Examiner* — Benjamin J Packard
(74) *Attorney, Agent, or Firm* — Myers Bigel, P.A.

(57) ABSTRACT

The present invention relates to bioinks based on undenatured collagen, kits containing the same, and methods of printing three-dimensional structures using the bioinks.

19 Claims, 5 Drawing Sheets

(51) Int. Cl.
 B33Y 10/00 (2015.01)
 B33Y 40/20 (2020.01)

(56) References Cited

FOREIGN PATENT DOCUMENTS

| WO | 2013/192290 | 12/2013 |
| WO | 2014/110590 | 7/2014 |
| WO | 2016/064648 | 4/2016 |
| WO | 2016092106 A1 | 6/2016 |

OTHER PUBLICATIONS

Park et al 2014 Biofabrication 6 035004 (Year: 2014).*
International Preliminary Report on Patentability corresponding to International Application No. PCT/US2017/056297 dated Apr. 25, 2019.
Extended European Search Report corresponding to European Application No. 17859555.9 dated Apr. 29, 2020.
Inzana et al. "3D printing of composite calcium phosphate and collagen scaffolds for bone regeneration", Biomaterials 35(13):4026-4034 (2014).
Tomlin et al. "Electrophoresis Studies of Tendon Collagen Solutions", Biochemica et Biophysica Acta 26(1):170-182 (1957).
"Office Action corresponding to Japanese Application No. 2019-519976 dated Feb. 10, 2022".
"Office Action corresponding to Japanese Application No. 2019-519976 dated Aug. 2, 2021".
"Office Action corresponding to Korean Application No. 10-2019-7010494 dated Sep. 29, 2021".
International Search Report and Written Opinion corresponding to International Application No. PCT/US2017/056297 dated Mar. 6, 2018.
Skardal A. et al. A hydrogel bioink toolkit for mimicking native tissue biochemical and mechanical properties in bioprinted tissue constructs. Acta Biamater, 2015, 25, pp. 24-34, (abstract) Retrieved from PubMed, PMID: 26210285.
"Office Action corresponding to Korean Application No. 10-2019-7010494 dated Jun. 13, 2022".
"Office Action corresponding to Japanese Application No. 2019-519976 dated Nov. 17, 2022".
"Office Action corresponding to Korean Application No. 10-2019-7010494 dated Oct. 27, 2022".
"Examination Report corresponding to European Application No. 17859555.9 dated Mar. 7, 2023".
"Office Action corresponding to Korean Application No. 10-2019-7010494 dated Jan. 19, 2023".
"Office Action corresponding to Canadian Application No. 3,037,280 dated Oct. 30, 2023".

* cited by examiner

THREE-DIMENSIONAL (3-D) PRINTING INKS MADE FROM NATURAL EXTRACELLULAR MATRIX MOLECULES

STATEMENT OF PRIORITY

The present invention is a 35 U.S.C. § 371 national phase application of PCT Application PCT/US2017/056297 filed Oct. 12, 2017, which claims the benefit, under 35 U.S.C. § 119(e), of U.S. Provisional Application No. 62/406,977, filed Oct. 12, 2016, and U.S. Provisional Application No. 62/536,727, filed Jul. 25, 2017, the entire contents of each of which are incorporated by reference herein in its entirety.

FIELD OF THE INVENTION

The present invention relates to bioinks based on undenatured collagen, kits containing the same, and methods of printing three-dimensional structures using the bioinks.

BACKGROUND OF THE INVENTION

Three-dimensional (3-D) printing has been a growing, dynamic field for 30 years. Early work began with laser sintering of powdered metal to form rough shapes that were then machined to final form. The technology has advanced so far that finished products are now manufactured with 3-D printers for commercial end use applications including surgical implants.

3-D bioprinting of biologic constructs began in the 1990's with laser sintering of powdered biocompatible thermoplastics and has evolved over the years to include inkjet printing approaches and precise extrusion techniques that build structures via addition of polymers that are then solidified into final structures via cooling, precipitation, drying, polymerization, or cross-linking. The most recent advances have been the introduction of 'bioinks' that permit 3-D printing of structures that include living cells. The most popular bioinks today include alginate, gelatin (denatured collagen), polyethylene glycol, and functionalized hyaluronic acid. These bioinks, combined with some of the earlier synthetic thermoplastics and selected cells, have been used to produce organoids with various cell types in near natural spatial orientations. However, the cells do not attach, migrate or differentiate the same in these structures as they do in the body.

Nearly all cells in the body are attached to extracellular matrix structures such as basement membranes, tendons, and bone. These extracellular structures have some influence on the cells and their behavior, and the cells in turn can resorb and replace extracellular matrix. The extracellular matrix (ECM) is composed of proteins such as collagens, fibronectin, vitronectin, and elastin and often proteoglycans like hyaluronic acid and chondroitin sulfate. These ECM molecules contain a number of different attachment sites and signaling motifs that allow various cells to attach and migrate and also signal various behaviors in the cells. The influence of the ECM has been key to cell biologists' ability to grow many fastidious cell types in culture. It has also been shown that implantation of ECM into animals promotes responses in vivo. For example, implantation of vascular tissue ECM promotes rapid migration of vascular endothelial and smooth muscle cells as well as stem cells that quickly colonize the ECM and then use it to rebuild new vascular structures.

There is strong interest today in bioinks that include ECM so that cells can attach, migrate, and remodel the 3-D printed structures. Gelatin has been tried. It will solidify into a gel at room temperature or below, but it liquefies at the higher temperatures preferred by cells (e.g., 37° C.). Thus, it must be chemically modified or mixed with other materials, allowing the gelatin to be crosslinked in order to maintain structure at 37° C. Gelatin can be methacrylated, printed into 3-D shapes and then crosslinked by exposure to UV light in the presence of a photoinitiator. Gelatin can be mixed with fibrinogen and exposed to thrombin for fibrin crosslinking. Gelatin can also be mixed with alginate and exposed to divalent salts for alginate crosslinking. Gelatin particles in solution are also useful as a support media when bioprinting with other bioinks. Hyaluronic acid modified with reactive groups has also been used in a similar manner.

Collagen is the predominant ECM molecule in the body and many cells have the ability to bind, migrate, resorb, and remodel it. There are at least 28 types of collagen with Type 1 being the most common. Like its denatured form, gelatin, collagen has been added at low concentrations to bioinks that gel at 37° C. to encourage cell attachment. However, at such low concentrations the density of cell attachment and signaling sites are unnaturally low, and the collagen is only able to contribute minimal structural integrity to the final 3-D structure.

Current bioinks containing ECM molecules have several shortcomings. Cells do not attach and behave normally on synthetic materials and they cannot resorb and replace the materials with natural ECM. ECM bioink formulations tested before now have not had the mechanical properties required for 3-D printing. Native materials to date lack the ability to shear thin and recover stiffness when printed. Neutralized collagen inks gel in the syringe and clog the printer.

The present invention addresses previous shortcomings in the art by providing bioinks made entirely or predominantly of collagen and methods of using the same.

SUMMARY OF THE INVENTION

The present invention relates to bioinks made entirely or predominantly of collagen. These bioinks can be mixed with cells, e.g., at neutral pH, and then printed into cell culture media. The bioinks provide superior working time and stiffness when printed in cell culture media.

Accordingly, one aspect of the invention relates to a bioink comprising undenatured collagen.

Another aspect of the invention relates to a bioink comprising undenatured collagen, wherein the bioink has a static stiffness of about 100 to about 150,000 Pa and a shear stiffness of less than about 50 Pa at a shear rate greater than 0.001 $\sec^{-1}$ at room temperature.

A further aspect of the invention relates to a bioink comprising undenatured collagen at a concentration of greater than 3 mg/ml, wherein collagen is the only extracellular matrix protein in the bioink.

An additional aspect of the invention relates to a bioink comprising undenatured neutralized collagen at a concentration of greater than 1 mg/ml and a crosslinker.

Another aspect of the invention relates to a bioink comprising undenatured collagen at a concentration of greater than 1 mg/ml, wherein the bioink gels at a temperature greater than 10° C. when neutralized.

A further aspect of the invention relates to a bioink comprising undenatured acidified collagen at a concentration of greater than 10 mg/ml.

An additional aspect of the invention relates to a bioink comprising undenatured precipitated collagen at a concentration of greater than 1 mg/ml.

Another aspect of the invention relates to a thixotropic bioink with a static stiffness of 100 to 150,000 Pa and a shear stiffness of less than about 50 Pa at a shear rate of greater than 0.001 sec$^{-1}$ that regains at least 20% of its static stiffness within 15 minutes of printing.

A further aspect of the invention relates to an undenatured collagen-based bioink that achieves a static stiffness of greater than 100 Pa within one minute of printing.

An additional aspect of the invention relates to a kit comprising a bioink of the invention.

Another aspect of the invention relates to a kit for preparation of a bioink wherein the kit comprises undenatured collagen.

Another aspect of the invention relates to a method of printing a 3-D structure comprising undenatured collagen, the method comprising using a bioink of the invention in a 3-D printer.

These and other aspects of the invention are set forth in more detail in the description of the invention below.

DETAILED DESCRIPTION OF THE INVENTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

Unless the context requires otherwise, throughout the present specification and claims, the word "comprise" and variations thereof, such as, "comprises" and "comprising" are to be construed in an open, inclusive sense, that is as "including, but not limited to."

By "consisting of" is meant including, and limited to, whatever follows the phrase "consisting of" Thus, the phrase "consisting of" indicates that the listed elements are required or mandatory, and that no other elements may be present.

The term "consists essentially of" (and grammatical variants), as applied to the compositions of this invention, means the composition can contain additional components as long as the additional components do not materially alter the composition. The term "materially altered," as applied to a composition, refers to an increase or decrease in the effectiveness of the composition of at least about 20% or more as compared to the effectiveness of a composition consisting of the recited components.

As used herein, the terms "function" and "functional," and the like, refer to a biological, enzymatic, or therapeutic function.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By "obtained from" is meant that a sample such as, for example, a cell or tissue, is isolated from, or derived from, a particular source, such as a desired organism or a specific tissue within a desired organism.

The term "extracellular matrix molecule" or "ECM" refers to macromolecules that are found in tissues outside of cells. These tissues perform many functions in the body such as basement membranes, scaffolding for organs, and the structure of tendons and ligaments. Collagens, fibronectin, vitronectin, elastin, chondroitin sulfate, heparan sulfate, and hyaluronic acid are common extracellular matrix molecules.

"Native collagen" is defined as collagen that retains normal conformation unlike gelatin that is collagen that has been irreversibly hydrolyzed.

"Gelatin" is defined as collagen that is >90%, e.g., >99% hydrolyzed or denatured.

"Collagen" is defined as a natural protein having the molecular structure known as atelocollagen, telocollagen, tropocollagen, procollagen, polymeric collagen, fibrillar collagen, electrospun collagen, insoluble collagen, soluble collagen, precipitated collagen, or collagen dough.

The term "undenatured collagen" refers to collagen that is less than 50% hydrolyzed or denatured, e.g., less than 50%, 45%, 40%, 35%, 30%, 25%, 20%, 15%, 10%, 9%, 8%, 7%, 6%, 5%, 4%, 3%, 2%, or 1% hydrolyzed or denatured.

"Bioink" is defined as cell compatible material that can be 3-D printed. Bioinks may be extruded through a needle between 0-37° C. and then can be gelled or solidified. They can be formulated for inkjet, laser-assisted, or microvalve 3-D printing equipment.

"Crosslink" is defined as chemically connecting macromolecules with covalent or ionic bonds.

"Predominantly" is defined as composing greater than 30%, e.g., greater than 30%, 40%, 50%, 60%, or 70% of the mass of solids in a solution or gel.

"Pure" is defined as composing greater than 70%, e.g., greater than 70%, 80%, 90%, 91%, 92%, 93%, 94%, 95%, 96%, 97%, 98%, or 99% of the mass of solids in a solution or gel.

"Toxic" is defined as an environment where less than 5% of cells in the environment still divide and replicate.

"Room temperature" is defined as about 15° C. to about 30° C.

"Light" is defined as electromagnetic radiation anywhere within the infrared through ultraviolet range.

"Thixotropic" is defined as the property exhibited by certain gels of becoming fluid when sheared (e.g., stirred or shaken) and returning to the semisolid state upon standing. For example, a thixotropic bioink is one in which viscosity or stiffness is reduced when sheared, but returns towards the original value over time when shearing stops.

The present invention relates generally to 3-D printing inks that are made from natural ECM molecules alone or mixed with synthetic materials. More specifically, these bioinks predominantly comprise, consist essentially of, or consist of ECM molecules including, but not limited to, type I collagen, other types of collagen, glycosaminoglycans such as hyaluronic acid and other ECM molecules. These bioinks have been formulated and produced in various concentrations, some fully native, some with chemical modifications, some with portions of the native extracellular matrix molecule removed and some mixed with synthetic materials. The various formulas and modifications have specifically been made to yield bioinks that are both of natural composition and lend themselves to being printed with 3-D printers. Lack of commercially available natural bioinks is the single greatest hurdle to the advancement of the 3-D bioprinting technology today.

In the bioinks of the present invention, cells behave more like they do naturally in the body. The cells within the bioink can remodel the scaffold, and the scaffold can be subsequently resorbed in vivo. Cells can attach and migrate through the structures. The cells easily survive the rigors of being 3-D printed with conventional 3-D printing equipment when combined with these natural bioinks. The natural bioink has the mechanical properties to allow the printing of 3-D constructs that hold shape and structure.

One aspect of the invention relates to a bioink comprising undenatured collagen. In some embodiments, the collagen may be any type I collagen. The most common sources of collagen I are rat tail, bovine skin and tendons or porcine skin. In some embodiments, the collagen is precipitated collagen. In some embodiments, collagen in solution is precipitated using increased ionic strength (salt concentration), pH and/or temperature. The precipitated collagen forms native-type fibrils which are then concentrated and resuspended in an isotonic saline solution. In some embodiments, the collagen is acidified collagen, e.g., having a pH<4.0, e.g., <3.5, 3.0, 2.5, or 2.0. The bioink may comprise more than one type of collagen. In some embodiments, the collagen is telocollagen, atelocollagen, or a combination thereof. In some embodiments, the collagen is the only ECM molecule (e.g., ECM protein or glycoprotein) in the bioink.

The bioink may be formed in a concentrated solution. In some embodiments, the undenatured collagen is present in the bioink at a concentration of greater than 1 mg/ml. In some embodiments, the undenatured collagen is at a concentration of greater than 3 mg/ml. In some embodiments, the undenatured collagen is at a concentration of greater than 5 mg/ml. In some embodiments, the undenatured collagen is at a concentration of greater than 10 mg/ml. In some embodiments, the undenatured collagen is at a concentration of greater than 1, 2, 3, 4, 5, 6, 7, 8, 9, 10, 11, 12, 13, 14, 15, 16, 17, 18, 19, 20, 25, 30, 35, 40, 45, or 50 mg/ml.

The bioink may have a static stiffness of about 100 to about 150,000 Pa, e.g., about 100, 200, 300, 400, 500, 600, 700, 800, 900, 1,000, 5,000, 10,000, 50,000, 100,000, or 150,000 Pa or any range therein. In some embodiments, the bioink achieves static stiffness of greater than 100 Pa, e.g., about 100, 200, 300, 400, 500, 600, 700, 800, 900, 1,000, 5,000, 10,000, 50,000, 100,000, or 150,000 Pa, within 1 minute of printing, e.g., within 5, 10, 15, 20, 25, 30, 35, 40, 45, 50, or 55 seconds or within 1, 2, 3, 4, or 5 minutes of printing.

In some embodiments, the bioink may have a shear stiffness of less than about 50 Pa, e.g., less than about 50, 45, 40, 35, 30, 25, 20, 15, 10, 5, or 1 Pa, at a shear rate greater than 0.001 sec$^{-1}$, e.g., at a shear rate greater than 0.01 or 0.1 sec$^{-1}$.

Another aspect of the invention relates to a bioink comprising undenatured collagen, wherein the bioink has a static stiffness of about 100 to about 150,000 Pa and a shear stiffness of less than about 50 Pa at a shear rate greater than 0.001 sec$^{-1}$ at room temperature.

A further aspect of the invention relates to a bioink comprising undenatured collagen at a concentration of greater than 3 mg/ml, wherein collagen is the only extracellular matrix protein in the bioink.

An additional aspect of the invention relates to a bioink comprising undenatured neutralized collagen at a concentration of greater than 1 mg/ml and a crosslinker.

Another aspect of the invention relates to a bioink comprising undenatured collagen at a concentration of greater than 1 mg/ml, wherein the bioink gels at a temperature greater than 10° C. when neutralized.

A further aspect of the invention relates to a bioink comprising undenatured acidified collagen at a concentration of greater than 10 mg/ml.

An additional aspect of the invention relates to a bioink comprising undenatured precipitated collagen at a concentration of greater than 1 mg/ml.

Another aspect of the invention relates to a thixotropic bioink with a static stiffness of 100 to 150,000 Pa and a shear stiffness of less than about 50 Pa at a shear rate of greater than 0.001 sec$^{-1}$ that regains at least 20%, e.g., at least 20%, 30%, 40%, 50%, 60%, 70%, 80%, or 90% of its static stiffness within 15 minutes of printing, e.g., within 1, 2, 3, 4, 5, 6, 7, 8, 9, 10, 15, or 20 minutes.

A further aspect of the invention relates to an undenatured collagen-based bioink that achieves a static stiffness of greater than 100 Pa within one minute of printing.

Collagen is temperature sensitive and, therefore, most sterilization procedures alter its fibrillar structure. Low mechanical properties, difficulties with sterilization and commonly observed shrinking of collagen scaffolds in response to cell activity are the main limitations of the material. In order to improve mechanical stability and decrease the degradation rate, collagen can be crosslinked, mixed with other polymers to form double networks, or with inorganic particles to form composite materials.

The collagen may be modified with chemical groups that permit crosslinking of the collagen. In some embodiments, the chemical groups permit crosslinking under conditions that are non-toxic for cells. Any suitable chemical group may be used. Examples of chemical groups include, without limitation, methacrylate, acrylate, divinyl sulfone, or a combination thereof.

In some embodiments, the collagen may be crosslinked without first being modified with chemical groups. The collagen may be crosslinked with a crosslinking agent. Any suitable crosslinking agent may be used. Examples include, without limitation, riboflavin, methacrylated gelatin (GelMA), polyethylene glycol diacrylate (PEGDA), alginate, fibrinogen and thrombin, glutaraldehyde, formaldehyde, genipin, an ammonium derivative, a photoinitiator, Irgacure®, lithium phenyl-2, 4, 6-trimethylbenzoylphosphinate (LAP), ruthenium, or any combination thereof. In some embodiments, the collagen may be crosslinked without chemical modification. In some embodiments, the collagen may be crosslinked with a photoinitiator and light exposure.

Irgacure® is a popular photoinitiator, but there are many other candidates. LAP is widely used and believed to be less toxic to cells than Irgacure®. It is activated with visible light. Methacrylated collagen is a very attractive crosslinker because the molecule is still undenatured and cells will attach to it and remodel it using native mechanisms (MMPs). Bioinks can also be crosslinked using PEGDA, though the molecule is quite inert and cells will not attach to it naturally. Collagen may also be crosslinked using light, heat, dehydration, aldehydes, genipin, and riboflavin.

The bioink may comprise one or more additives. In some embodiments, the additive may be a crosslinker, a stiffener, a synthetic material, or any combination thereof. Examples of crosslinkers include, without limitation, riboflavin, GelMA, PEGDA, alginate, glutaraldehyde, formaldehyde, genipin, an ammonium derivative, a photoinitiator, Irgacure®, LAP, ruthenium, or any combination thereof. Examples of stiffeners include, without limitation, carbon nanotube, carbon fiber, bioglass, calcium phosphate ceramic, nanocellulose, carbon nano-brush, or any combination thereof.

The additive may be, for example, a protein, glycosaminoglycan, growth factor, or any combination thereof. In some embodiments, the additive may be an ECM molecule, decellularized tissue, or a combination thereof. The ECM molecule or decellularized tissue may be from any tissue or organ, such as heart, lung, kidney, liver, skin, placenta, intestine, or bladder tissue. The ECM molecule or decellularized tissue may optionally be solubilized. In some embodiments, the collagen is the only ECM molecule in the bioink. In certain embodiments, the bioink may comprise different ECM molecules. In some embodiments, the different ECM molecule may be hyaluronic acid. In some embodiments, the bioink may comprise cells. The bioink may comprise one or more types of cells.

Due to the differences among tissues within the body, it is unlikely that one standard bioink can be used to print all the different tissues. There is a need to add additional proteins to the bioink to create a custom bioink for the specific tissue being printed. To add additional ECM molecules, the ECM molecule can be added to the cell culture media/cell suspension that will be added to the ink. The combination can be added to a syringe, the syringe coupled to the syringe with the bioink, and then mixed back and forth, e.g., >40 times, to ensure thorough mixing.

This same technique can be used to add crosslinking agents to the bioink. These crosslinkers can include acrylate modified polyethylene glycol, methacrylated gelatin, methacrylated hyaluronic acid, genipin, riboflavin, glutaraldehyde, formaldehyde and macromolecules modified with other crosslinkable groups such as acrylate or divinyl sulfone. This same technique can also be used to add bioink stiffening agents, such as bioglass, carbon nanotubes, nanobrushes, or cellulose.

In some embodiments, the bioink may comprise a liquid carrier. In some embodiments, the bioink comprises physiological salts, buffers, and/or other components that support cell survival.

The bioink may be at a basic pH, at a neutral pH, or at an acidic pH.

In some embodiments, the bioink is sterile. In some embodiments, the bioink comprises antibiotics or other agents that promote a sterile condition. Bioprinted structures that are cultured with cells are preferably sterile. This requirement can occasionally be provided with the use of antimicrobials. However, it is relatively easy to sterilize collagen-based bioinks by lowering their pH to less than 4.6 then neutralizing them prior to mixing with cells. They can also be sterilized by filtration then aseptic processing to arrive at the desired concentration. Bioburden may also be reduced using irradiation (UV, E-beam, gamma) or ozone.

In some embodiments, the bioink has a viscosity suitable for extrusion through a nozzle or orifice. In some embodiments, the nozzle or orifice has a diameter of less than 250 μm, e.g., less than 250, 225, 200, 175, 150, 125, or 100 μm.

In some embodiments, the bioink of the present invention may be used to print 3-D structures at room temperature.

Another aspect of the invention relates to a kit comprising a bioink of the invention. The kit may comprise one or more containers of the bioink. In some embodiments, the kit may comprise additional components, such as a syringe, a syringe coupler, an additive, a buffer, a solvent, a neutralization solution, a crosslinker solution, or any combination thereof.

Another aspect of the invention relates to a kit for preparation of a bioink of the invention, e.g., comprising components to be mixed together to provide fresh bioink. In some embodiments, the kit may comprise undenatured collagen. In some embodiments, the collagen is precipitated collagen. In some embodiments, the collagen may be modified with chemical groups that permit crosslinking. In some embodiments, the kit may comprise an additive, a buffer, a solvent, a neutralization solution, a crosslinker solution, or any combination thereof.

Another aspect of the invention relates to a method of printing a 3-D structure comprising undenatured collagen. The method may comprise using a bioink of the invention in a 3-D printer. Methods of using 3-D printers are well known in the art. The 3-D printer may be any 3-D printer currently available or developed later, e.g., an inkjet printer, a robotic dispensing printer, an extrusion-based printer, or a laser-based printer.

Inkjet printing is a non-contact strategy based on the deposition of bioink drops in a predesigned manner to form a final multilayer pattern. Robotic dispensing printing can be continuous extrusion where the ink is dispensed by a pneumatic or mechanical force or microvalve-based droplet ejection which is a technique between inkjet and standard extrusion techniques. Laser-based printing is based on the transfer of a bioink from a donor substrate to a receiving substrate controlled by laser beam pulses that target a precisely defined position.

In some embodiments, the method may comprise crosslinking of the 3-D structure as the 3-D structure is being printed, e.g., before printing of the structure is finished. In some embodiments, the method may comprise crosslinking of the 3-D structure after the 3-D structure is printed.

In some embodiments, the method may comprise changing the temperature of the 3-D structure as the 3-D structure is being printed. In some embodiments, the method may comprise changing the temperature of the 3-D structure occurs after the 3-D structure is printed. Temperature changes may be, for example, from a cooler temperature (e.g., 0-10° C. or 20-30° C. or room temperature) to a warmer temperature (e.g., 35-40° C. or 37° C.) to promote gelling and/or crosslinking of the structure.

In some embodiments, the method may comprise changing the pH of the 3-D structure as the 3-D structure is being printed. In some embodiments, the method may comprise changing the pH of the 3-D structure after the 3-D structure is printed. pH changes may be, for example, from an acidic or basic pH to a neutral pH to promote gelling and/or crosslinking of the structure. pH can be changed, for example, by having a buffer present in the media the structure is printed into.

In some embodiments, the method may comprise exposing the 3-D structure to light as the 3-D structure is being printed. In some embodiments, the method may comprise exposing the 3-D structure to light after the 3-D structure is printed. The light may be, for example, ultraviolet, visible, or infrared light to promote gelling and/or crosslinking of the structure, e.g., in the presence of a photoinitiator.

In some embodiments, the method may comprise adding cells to the 3-D structure as the 3-D structure is being printed. In some embodiments, the method may comprise adding cells to the 3-D structure after the 3-D structure is printed. In some embodiments, the method may comprise printing cells on the 3-D structure during or after printing. For example, a 3-D printer with two or more nozzles may alternately or in some other pattern print a layer of bioink and a layer of cells. In some embodiments, the cells are incubated with the 3-D structure after the 3-D structure is printed so that cells may migrate onto or into the structure.

To best mimic a cell's native environment with 3-D bioprinting, multiple extruders are often employed. Each extruder can be filled with a different bioink and cell type, to allow the printing of multiple layers of tissues. The multi-head system can also be used to print a structural scaffold out of a synthetic material with one head, and then fill it in with a native material with another extruder.

The bioink may be printed into a support media or bath. In some embodiments, the support media comprises nutrients for cells. In some embodiments, the support media provides temporary support to the 3-D structure, e.g., until the structure gels or is crosslinked. The temporary support may be provided by a support agent in the media, such as, without limitation, a gelatin slurry, a slurry of hydrogel particles, or a slurry of hydrophilic particles.

Figure 1:
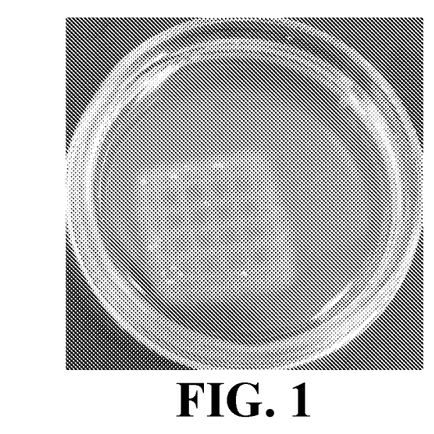
FIG. 1 shows a lattice printed on a custom-built 3-D printer using TeloCol® bioink neutralized and printed into a support bath.

The first collagen breakthrough for the present invention came with the use of TeloCol® type I bovine collagen at 3 mg/ml. The collagen can be solubilized by acidification to pH<4 and chilling to 1-10° C. Cells are added to the bioink by chilling the cells to <10° C. and mixing with the collagen in enough cell culture media to neutralize the collagen or by adding sufficient base to neutralize the collagen immediately prior to mixing with the chilled cell solution. This bioink can then be loaded into a 3-D printer and extruded into the desired structure. The bioink quickly gels when it warms above 10° C. such as when printed into warm cell culture media. Complex structures with excellent resolution can be printed with this bioink as shown in FIG. 1. Thus, the first useful bioink composed of pure undenatured collagen was successfully prepared. However, the bioink must be maintained at 1-10° C. or it will gel in the printer, and few 3-D printers are able to keep the bioink that cold. As a result, the working time for printing 3-D structures is often 10 minutes or less using this bioink formulation.

Figure 2:
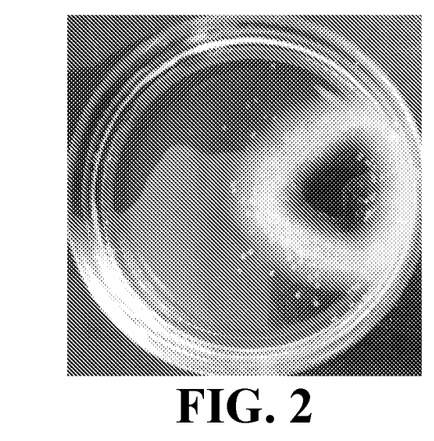
FIG. 2 shows an aortic ring printed on a custom-built 3-D printer using FibriCol® bioink, neutralized and printed into a chilled support bath.

To overcome this working time limitation a new bioink was developed from FibriCol® that is a concentrated, undenatured, atelo-peptide Type I collagen solution. FibriCol can be neutralized, yet not begin to gel at room temperature. Upon warming to 37° C., it will form a stiff gel. This material was much easier to use and worked reasonably well, but had low resolution when printing because the collagen would diffuse into the cell culture media until it was warmed and gelled. See FIG. 2.

Figure 3:
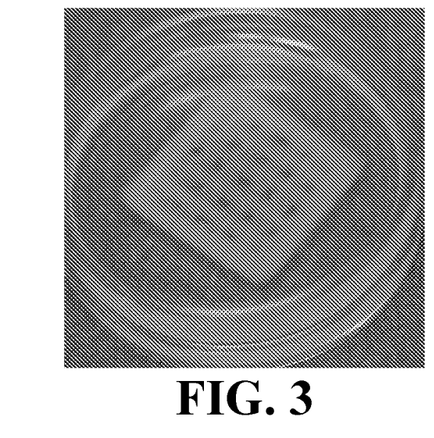
FIG. 3 shows a lattice printed on a custom-built 3-D printer using methacrylated collagen bioink, printed into a neutralized chilled support bath and then UV-crosslinked.

To overcome the diffusion problem, a bioink was developed from PhotoCol®, a type I methacrylated bovine collagen. The base material is telocollagen, and thus gels quickly when neutralized. This material was printed as a concentrated (10 mg/ml) acidic solution into a neutral buffer, which neutralized the collagen and allowed the gel formation to begin. To help limit diffusion, the collagen was UV-crosslinked upon extrusion, due to the reactive methacrylate sites on the collagen molecule. See FIG. 3. The UV crosslinking instantly strengthens the collagen and limits diffusion. This material is easy to work with and gives good printing resolution. Cells can be cultured on the structures and allowed to infiltrate into the collagen after crosslinking.

Figure 5:
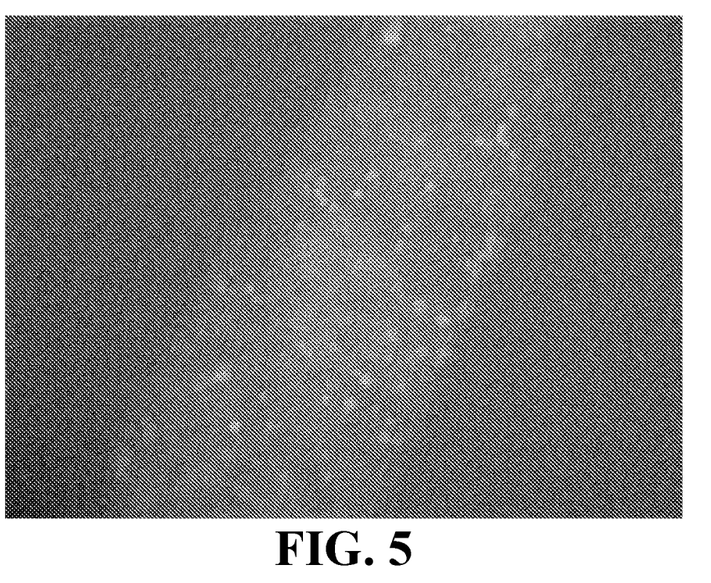
FIG. 5 shows human adipose-derived stem cells printed in collagen gel. The width of the printed filament is 160 microns.

Advanced Biomatrix sells such a collagen (part number BRD5201) with 25-40% of the lysine groups methacrylated. Bioinks made with 3 to 10 mg/ml of this collagen in solution with 10-50 ppm Irgacure® 2959 and crosslinked with UV light (365 nm wavelength) form gels with elastic modulus ranging from 200 to 8000 Pa. This crosslinkable collagen can be mixed with other collagens, other extracellular matrix molecules, decellularized tissue, or even synthetic materials. FIG. 5 shows the viability of fibroblasts 2 days after printing in a blend of methacrylated collagen with pure, undenatured Type 1 collagen.

It would be advantageous in many situations to use a bioink that is pH neutral so cells can be added to the ink, but does not quickly gel at room temperature. Typically, increasing the concentration of collagen increases the speed of gelation and the stiffness of the resulting gel. Once a collagen solution has gelled it breaks if the shear force is greater than the gel stiffness. If you try to mix cells into the gel you get islands of gelled collagen and regions with cells in solution. If you extrude gelled collagen through a fine needle you get spurts of solution with frequent breaks in the filament.

Figure 4:
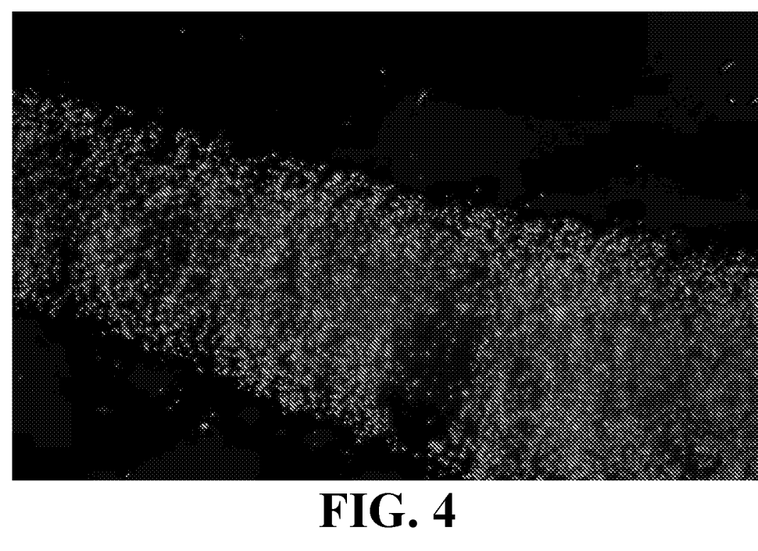
FIG. 4 shows the viability of human adipose-derived stem cells immediately after printing. The green cells are viable, while the red stained cells have died. The high ratio of live:dead indicate that the collagen bioink is shear thinning and the cells are able to be extruded without significant damage.
Figure 6:
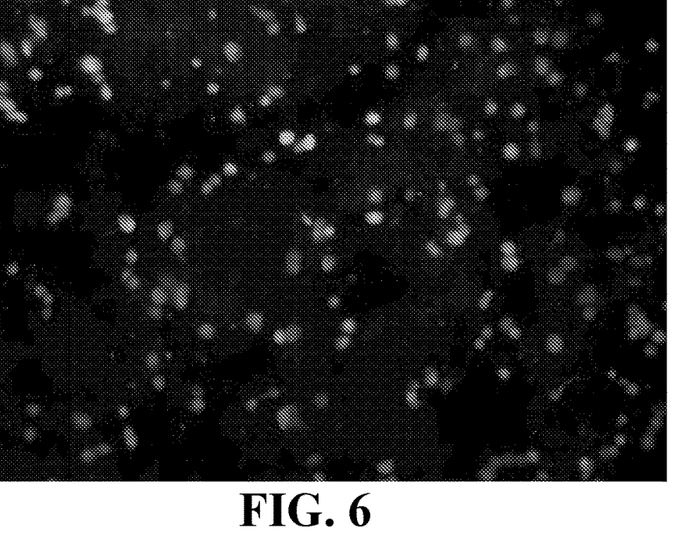
FIG. 6 shows human fibroblasts 3-D bioprinted in LifeInk® 200 after 2 days of culture. The high green:red (live:dead) ratio indicates high cell viability.

Surprisingly, it was found that a gel of concentrated, precipitated collagen worked very well. This bioink, known as LifeInk® 200, can be purchased from Advanced Biomatrix (Carlsbad, CA) with part number #5202-1EA. This material maintains a strong filament during extrusion, with little to no diffusion when printing into a support bath. When mixed or extruded through a print nozzle, the elastic modulus drops to under 1 Pa. After leaving the nozzle, the gel regains most of its original gel strength, and at 37° C., will form a gel with an elastic modulus of about 1000 Pa, showing that this gel will shear thin and quickly recover. This shear-thinning property allows cells to be mixed and then extruded through the nozzle without damage as illustrated in FIG. 4. Once the bioink has been extruded it again gels and retains its shape with high fidelity as seen in FIG. 5. This ink can be stored and used at neutral pH and mixed with cells and printed at temperatures up to at least 38.5° C. Cells printed in LifeInk® 200 thrive in the native collagen environment, as seen in FIG. 6.

The present invention is explained in greater detail in the following non-limiting Examples.

Example 1

Methacrylated Collagen Bioink (LifeInk® 100)

Type I Collagen with telo-peptides with 40% of lysines methacrylated and then lyophilized (Advanced Biomatrix part number BRD5201) was solubilized in 20 mM acetic acid at a concentration of 8 mg/ml. The solution was then cooled to 2° C. and neutralized with cold alkaline phosphate buffered saline. Irgacure® 2959 was added to make a 20 ppm solution and the solution was poured into a dish and gelled at 37° C. After gelling for 15 minutes the solution was crosslinked with UV light for 5 minutes. The stiffness of the gel was measured on a Bohlin rheometer (DVO-100) and found to be 6000 Pa.

Example 2

Pure Collagen Bioink (LifeInk® 200)

Figure 7:
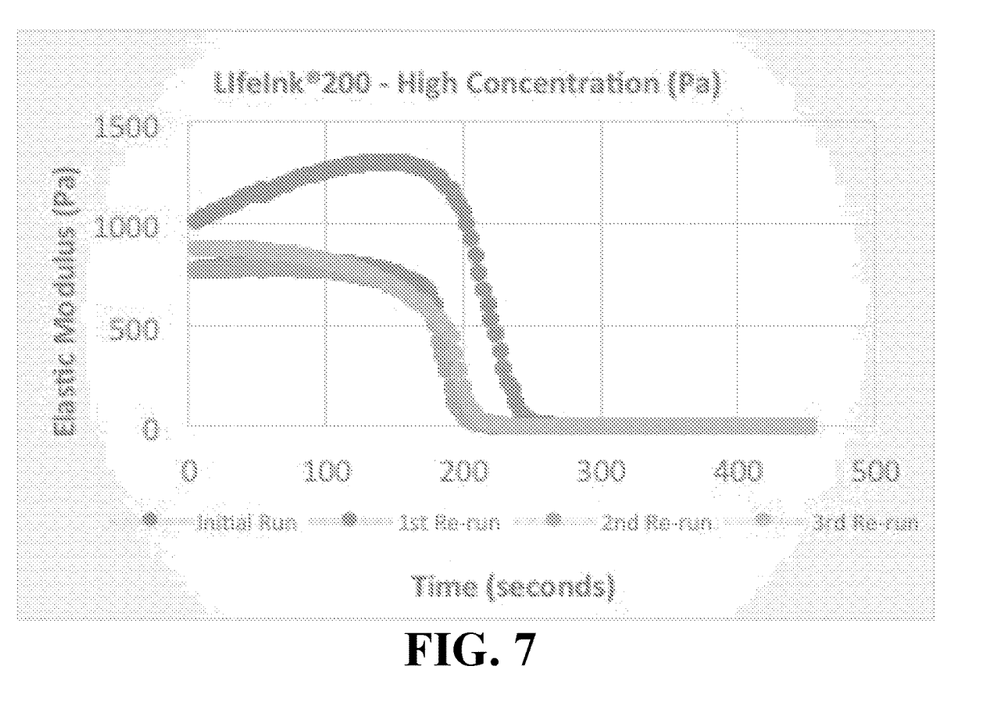
FIG. 7 shows shear thinning properties of a pure, undenatured collagen gel at high concentration.

Type I Collagen without telo-peptides was prepared at high concentration by precipitation. This collagen can be obtained from Advanced Biomatrix (part number #5202-1EA). This solution was poured into a dish and allowed to gel at 37° C. for 30 minutes before testing on a Bohlin rheometer. The gel initially had a stiffness of 1300 Pa, but it drops to a very low value when sheared at a rather low rate. When the shear force is removed the gel resumed its initial high stiffness. The process was found to be repeatable over multiple cycles with 15 minutes intervals between each test as shown in FIG. 7.

Example 3

Printing with Pure Collagen Bioink (LifeInk® 200)

Figure 8:
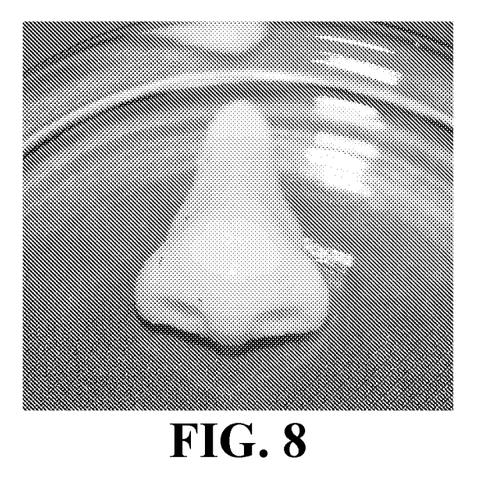
FIG. 8 shows a nose 3-D bioprinted using pure collagen bioink, LifeInk® 200.

LifeInk® 200 from Advanced BioMatrix (part number #5202-1EA) was printed using a pneumatic based extrusion printer to create a nose representation. The collagen bioink was printed at room temperature over the course of an hour. The extruder pressure was <30 psi at all times, and the bioink was extruded through a 30 gauge needle with a final resolution of ~160 micrometers. The final printed structure was >30 mm long and 10 mm high (FIG. 8). The structure held its shape in cell culture media for over 6 months.

Example 4

Printing a Mixture of Pure Collagen and Gelatin Methacrylate

Figure 9:
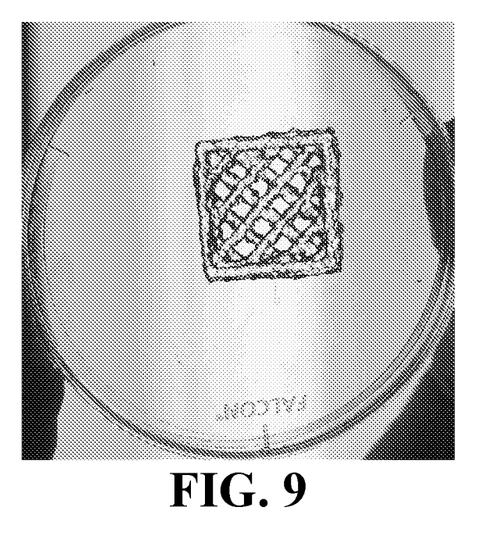
FIG. 9 shows a 10 layer tall structure of methacrylated gelatin mixed with precipitated collagen, printed and UV-crosslinked.

LifeInk® 200 from Advanced BioMatrix (part number #5202-1EA) was left at room temperature for 10 minutes. Irgacure® 2959 was added to methacrylated gelatin in solution that had been warmed to 35° C. 5 mL of methacrylated gelatin was pipetted into a syringe and allowed to cool to <30° C. The methacrylated gelatin syringe was coupled to the LifeInk® 200 collagen bioink, and then mixed back and forth >40 times to ensure thorough mixing. This created a 1:1 mixture of collagen to methacrylated gelatin. The resulting mixture was printed on a pneumatic printer and was able to create a structure 10 layers high (FIG. 9). UV light was used to cure the printed structure.

Example 5

Crosslinking Collagen with Riboflavin

FibriCol® from Advanced BioMatrix (part number #5133-20ML) was neutralized and dispensed into a dish and incubated at 37° C. for 30 minutes. The gel stiffness of the sample was then measured on a Bohlin rheometer. Another sample of FibriCol® was mixed with riboflavin. The material was placed into a dish, and allowed to gel at 37° C. After 30 minutes, this sample was placed in a UV chamber and exposed to UV-light for 5 minutes. The gel stiffness was measured on a Bohlin rheometer. Table 1 shows the increase in gel stiffness by incorporating riboflavin (a crosslinker) into the collagen bioink.

TABLE 1

| Gel stiffness of FibriCol with and without riboflavin/UV crosslinking | |
|---|---|
| Condition | Gel Stiffness |
| Gelled FibriCol with no riboflavin | 616 Pa (average of 2 tests) |
| FibriCol with riboflavin (0.02%) added into the collagen prior to collagen gelation-UV treatment (365 nm for 5 minutes) | 1623 Pa (average of 5 tests) |

Example 6

Adding Hyaluronic Acid to Pure Collagen Bioink 0.85 mL of 3% hyaluronic acid with a molecular weight of 1,300,000 Da and 1.15 mL of cell culture media was added to 5 mL of LifeInk® 200 from Advanced BioMatrix (part number #5202-1EA). The resulting bioink was more similar to natural ECM, being comprised of ~12% glycosaminoglycans, and 88% type I collagen. The bioink mixture was then extruded through a 30 gauge needle and the resulting filament strength was compared to the filament strength of just LifeInk® 200. The filaments were comparable in strength fidelity and the bioink mixture demonstrated comparable printability.

Example 7

Adding Bioactive Glass to Pure Collagen Bioink

Figure 10:
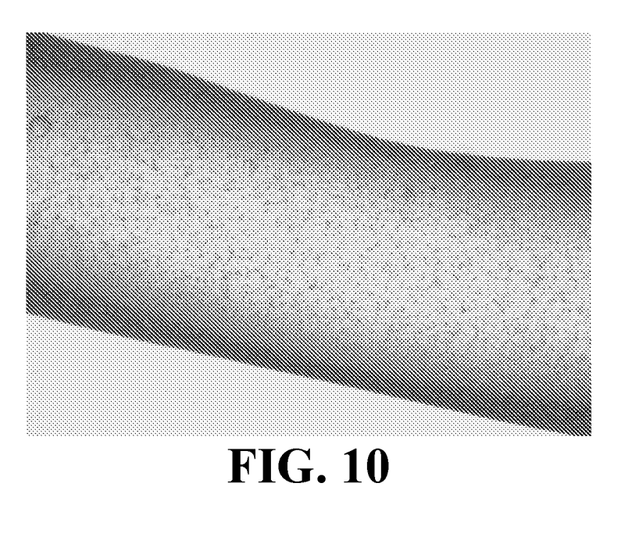
FIG. 10 shows a microscope image (5×) of bioglass fully dispersed throughout LifeInk® 200 collagen bioink in a 30:70 ratio, after being successfully 3-D bioprinted through a 30 gauge needle.

Bioactive glass needs to be suspended in a viscous material for 3-D bioprinting to prevent settling of the glass into the needle and causing clogging. Bioactive glass was added to LifeInk® 200 in various ratios (10:90, 30:70, 65:35 glass/collagen) and 3-D bioprinted through a 30 gauge needle into a support bath (FIG. 10). The resulting material can be subjected to simulated body fluids and turn into hydroxyapatite. This new environment is ideal for osteoblasts to produce bone.

Example 8

Bioprinting with pH Neutral 10 mg/ml Type I Atelocollagen

FibriCol® from Advanced BioMatrix (catalog #5133-20ML) is a 10 mg/ml concentration type I atelocollagen. This material was neutralized and printed at room temperature into a support media. The atelocollagen allows printing at room temperature without gelation prior to printing. Once printed, the structure was incubated at 37° C. to allow thermal gelation of the collagen. The gel strength of the collagen was 1000 Pa after 30 minutes of incubation.

Example 9

Bioprinting with pH Neutral 3 mg/ml Type I Telocollagen

Figure 11:
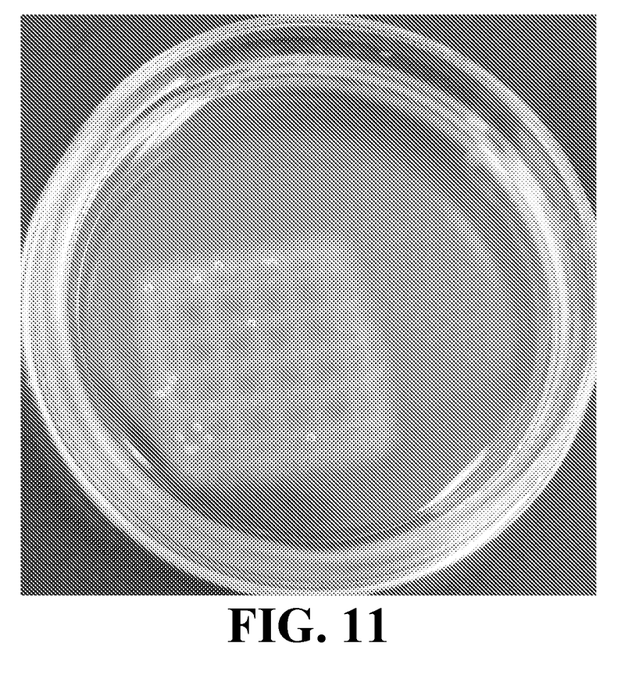
FIG. 11 shows a TeloCol® telocollagen printed structure at 3 mg/ml.

TeloCol® from Advanced BioMatrix (5026-50ML) is a 3 mg/ml telocollagen. This material was neutralized and printed in a cold environment (<10° C.) to prevent gelation of the collagen in the syringe prior to printing. The material was printed into a room temperature support bath, allowing the collagen to gel upon printing. After printing the structure was placed in the incubator at 37° C. for 30 minutes to allow additional gelation (FIG. 11).

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

That which is claimed is:

1. A bioink comprising undenatured collagen at a concentration of greater than 20 mg/ml, wherein the bioink comprises less than 10% denatured collagen, and wherein the bioink has a static stiffness of about 100 to about 150,000 Pa and a shear stiffness of less than about 50 Pa at a shear rate greater than 0.001 sec$^{-1}$ at room temperature.

2. The bioink of claim 1, wherein the bioink gels at a temperature greater than 10° C. when neutralized.

3. The bioink of claim 1, wherein the collagen is a type I collagen.

4. The bioink of claim 1, wherein the collagen is telocollagen, atelocollagen, or a mixture thereof.

5. The bioink of claim 1, comprising more than one type of collagen.

6. The bioink of claim 1, wherein collagen is the only extracellular matrix protein in the bioink.

7. The bioink of claim 1, wherein the collagen is modified with chemical groups that permit crosslinking of the collagen.

8. The bioink of claim 1, wherein the collagen can be crosslinked without chemical modification of the collagen, optionally with a photoinitiator and light exposure.

9. The bioink of claim 8, wherein the collagen can be crosslinked with a photoinitiator and light exposure.

10. The bioink of claim 1, further comprising an additive, optionally a crosslinker, a stiffener, a synthetic material, or any combination thereof.

11. The bioink of claim 10, wherein the additive is a protein, glycosaminoglycan, growth factor, or any combination thereof or wherein the additive is an extracellular matrix molecule, decellularized tissue, or any combination thereof.

12. The bioink of claim 1, wherein the bioink further comprises a different extracellular matrix molecule.

13. The bioink of claim 1, wherein the bioink further comprises cells.

14. The bioink of claim 1, wherein the bioink can be used to print 3-D structures at room temperature.

15. A thixotropic bioink comprising undenatured collagen at a concentration of greater than 20 mg/ml, with a static stiffness of 100 to 150,000 Pa and a shear stiffness of less than about 50 Pa at a shear rate of greater than 0.001 sec$^{-1}$ that regains at least 20% of its static stiffness within 15 minutes of printing.

16. A kit for preparation of the bioink of claim 1, the kit comprising undenatured collagen, wherein the undenatured collagen is present in a solution at a concentration of greater than 20 mg/ml.

17. A method of printing a 3-D structure comprising undenatured collagen, the method comprising using the bioink of claim 1 in a 3-D printer.

18. The method of claim 17, further comprising crosslinking the 3-D structure as it is printed or after it is printed or changing the temperature of the 3-D structure as it is printed or after it is printed or exposing the 3-D structure to light as it is printed or after it is printed.

19. The method of claim 17, wherein the bioink is printed into a support media, optionally wherein the support media provides temporary support to the 3-D structure, optionally wherein the temporary support is provided by a slurry of hydrogel particles.

* * * * *

UNITED STATES PATENT AND TRADEMARK OFFICE
CERTIFICATE OF CORRECTION

PATENT NO. : 11,850,324 B2
APPLICATION NO. : 16/341360
DATED : December 26, 2023
INVENTOR(S) : Bagley et al.

It is certified that error appears in the above-identified patent and that said Letters Patent is hereby corrected as shown below:

In the Specification

Column 13, Line 43: Please correct "1000 Pa" to read --~1000 Pa--

Signed and Sealed this
Nineteenth Day of March, 2024

Katherine Kelly Vidal
*Director of the United States Patent and Trademark Office*